(12) United States Patent
Koverech et al.

(10) Patent No.: US 8,377,988 B2
(45) Date of Patent: *Feb. 19, 2013

(54) USE OF L-CARNITINE OR OF ALKANOYL L-CARNITINES FOR THE PREPARATION OF A PHYSIOLOGICAL SUPPLEMENT OR MEDICAMENT FOR OPHTHALMIC USE IN THE FORM OF EYE DROPS

(75) Inventors: Aleardo Koverech, Rome (IT); Nicola Pescosolido, Rome (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 25 days.

This patent is subject to a terminal disclaimer.

(21) Appl. No.: 12/641,687

(22) Filed: Dec. 18, 2009

(65) Prior Publication Data

US 2010/0093858 A1   Apr. 15, 2010

Related U.S. Application Data

(63) Continuation of application No. 11/570,662, filed on Dec. 14, 2006, now Pat. No. 7,655,698, and a continuation-in-part of application No. PCT/EP2006/062919, filed on Jun. 6, 2006.

(30) Foreign Application Priority Data

Jul. 1, 2005   (EP) .................................... 05014337

(51) Int. Cl.
  *A61K 31/197*   (2006.01)
  *A61K 31/221*   (2006.01)
(52) U.S. Cl. ........................................ 514/547; 514/516
(58) Field of Classification Search .................. None
  See application file for complete search history.

(56) References Cited

U.S. PATENT DOCUMENTS

| 4,775,531 | A | 10/1988 | Gilbard |
| 4,897,421 | A | 1/1990 | Braquet |
| 5,403,598 | A * | 4/1995 | Beck et al. .................... 424/717 |
| 5,817,630 | A * | 10/1998 | Hofmann et al. ............ 514/20.8 |
| 6,585,987 | B1 * | 7/2003 | Fransoni ........................ 424/401 |
| 6,812,251 | B2 | 11/2004 | Calabresi et al. |
| 7,655,698 | B2 | 2/2010 | Koverech et al. |
| 2001/0041671 | A1 | 11/2001 | Napoli |
| 2002/0017305 | A1* | 2/2002 | Bagrov et al. ................. 128/898 |
| 2006/0035842 | A1 | 2/2006 | Tsuzuki et al. |

FOREIGN PATENT DOCUMENTS

| WO | 95/05804 | 3/1995 |
| WO | 00/29030 | 5/2000 |

OTHER PUBLICATIONS

Koyama et al (Adv Exp Med Biol 403:9-18, 1996).*
Sieradzki et al (Klin Oczna 100:85-88, 1998; Abstract only).*
Frey et al (Am J Ophthalmol 92(4):559-67, 1981).*
Ludwig and Van Ooteghem (J Pharm Belg 42:259-266, 1987).*
Frey et al. (Am J Ophthalmol 92(4):559-67, 1981).
Koyama et al. (Adv Exp Med Biol 403:9-18, 1996).
Sieradzki et al. (Klin Oczna 100:85-88, 1998).
Cuisinier et al. (Eur J Appl Physiol 87:489-495, 2002).
Miyazawa et al. (Ann NY Acad Sci, 1031:401-404, 2004).
McNairn (Can Fam Physician 25:952-957), (1979).
Eby and Halcomb (Med Hypotheses 17:157-165, 1985).
Stevenson et al. (Ophthalmology 107:967-974, 2000).
Aragona, P et al. (Br J Ophthalmol 86:879-884, 2002).
Asbell et al (Dry Eye Disease, Chapter 7, 2006).

\* cited by examiner

*Primary Examiner* — Craig Ricci
(74) *Attorney, Agent, or Firm* — Lucas & Mercanti, LLP

(57) ABSTRACT

Use of L-carnitine and/or of one or more alkanoyl L-carnitines or one of their pharmaceutically acceptable salts for the preparation of an ophthalmic physiological supplement or medicament in the form of eye-drops, for the treatment of corneal diseases.

2 Claims, No Drawings

USE OF L-CARNITINE OR OF ALKANOYL L-CARNITINES FOR THE PREPARATION OF A PHYSIOLOGICAL SUPPLEMENT OR MEDICAMENT FOR OPHTHALMIC USE IN THE FORM OF EYE DROPS

CROSS-REFERENCE TO RELATED APPLICATIONS

This application is a continuation of U.S. application Ser. No. 11/570,662 filed Dec. 14, 2006, which is a continuation-in-part of PCT/EP2006/062919, filed Jun. 6, 2006, the contents of each of which are incorporated herein by reference. This application also claims the benefit of priority therefrom.

FIELD OF THE INVENTION

The present invention relates to the use of L-carnitine and/or one or more alkanoyl L-carnitines for the preparation of a physiological supplement or medicament in the form of eyedrops useful for the treatment of corneal diseases.

BACKGROUND OF THE INVENTION

The cornea is the transparent, dome-shaped window covering the front of the eye. It is a powerful refracting surface, providing ⅔ of the eye's focusing power. Like the crystal on a watch, it gives us a clear window to look through.

The cornea is extremely sensitive—there are more nerve endings in the cornea than anywhere else in the body.

The adult cornea is only about ½ millimeter thick and is arranged in three main regions, or layers:

Epithelium: it functions primarily to block the passage of foreign material such as dust or water into the eye, and other layers of the cornea, and provide a smooth surface that absorbs oxygen and other needed cell nutrients that are contained in tears. This layer, which is about five cells deep, is filled with thousands of tiny nerve endings that make the cornea extremely sensitive to pain when rubbed or scratched.

Stroma: is located behind the epithelium, the stroma comprises about 90 percent of the cornea. It consists primarily of water and layered protein fibers that give the cornea its strength, elasticity, and form; and cells that nourish it. The unique shape, arrangement, and spacing of the protein fibers are essential in producing the cornea's light-conducting transparency.

Endothelium: this single layer of cells is located between the stroma and the aqueous humor. Because the stroma tends to absorb water, the endothelium's primary task is to pump excess water out of the stroma. Without this pumping action, the stroma would swell with water, become hazy, and ultimately opaque.

Many diseases can damage this delicate structures.

The main causes of impairment of the epithelial structure of the cornea are dry eye syndrome; corneal abrasions and injuries due to, for example, the application of contact lenses; and refractive laser surgery.

Other diseases of the cornea are associated with impairment of the normal transparency of the corneal surface, caused, for example, by damage in the aftermath of keratitis, particularly bacterial, viral or fungal keratitis; by damage resulting from trauma and refractive laser surgery; as well as degenerative or hereditary diseases such as chronic and acute keratoconus.

The tear film, which coats the corneal epithelium and is essential for the homeostasis of the eye surface, performs an important optical function, acting as a lubricant between the eyelids and the eyeball and as a vehicle for oxygen, guaranteeing the metabolism of the cells of the corneal epithelium; it also performs a flushing function, ensuring the removal of external agents. The normal tear osmolality in adult (human) is about 300±10.0 mOsm/kg and is not significantly affected by age (Optom. Vis. Sci. 1995, vol 72, n° 10, 713-717).

The tear film is also important for its function as a carrier for growth factors, neuropeptides, and neuromodulators that regulate the activation, proliferation and differentiation of corneal and conjunctival epithelial cells. It also transports immunoglobulins (IgA, IgAs, IgG, IgE, IgM), complement factors (C3, C4, C5), metalloproteases (MMP-2, 4, 9), enzymes (lysozyme, lactoferrin) and immune system cells (lymphocyte), thus performing a fundamental defensive function against infections.

Dry eye syndrome is characterised by a quantitative (hypolacrimation) and/or qualitative (dyslacrimation) impairment of the tear film of multifactorial origin which may or may not cause clinically significant damage to the eye surface. The prevalence of dry eye syndrome ranges from 10 to 40% in the adult population and there is a highly significant correlation with age.

In the United States, the prevalence of mild-to-moderate dry eye syndrome is up to approximately 10 million people (*Am. J. Ophthalmol:,* 1997; 124:723-728; *Arch Ophthalmol.,* 2000; 118: 1264-1268).

Various studies conducted in order to understand the mechanisms activated in this disease have shown that the tears of subjects affected by dry eye syndrome present: an increased evaporation rate, increased surface tension, reduced vitamin A concentration, increased osmolality, reduced concentration of a number of proteins (lysozyme, lactoferrin), insufficient mucus production or qualitative changes in mucus production, with consequent inadequate reconstruction of the mucus layer, reductions in a number of growth factors (EGF, TGF-α, aFGF-bFGF, LG-F, HGF) (*Contactologia,* 1982; 4: 34-37), changes in concentration of inorganic elements, reduced androgens and dysregulation of T lymphocyte activity (*Cornea,* 2005; 24: 1-7). Among the mechanisms activated in this disease the use of contact lenses has to be mentioned.

The clinical signs regarded as being most closely related to this pathological condition are reduced break-up time (BUT test) and Schirmer test results (*Pescosolido N.: Le alterazioni del film lacrimale. In Stendler P.: "il sistema lacrimale", Fabiano editore, Canelli (AT),* 2000; pag. 237-330; hereinafter this reference will be referred to as *Pescosolido* 2000).

The BUT test has to do with the mucin content of the tear film and, in the dry eye, yields only values below 5 seconds. The Schirmer test, on the other hand, has to do with the water content of the tear film and, in the dry eye, yields values below 5 millimeters in 5 minutes.

The patient presents the following symptoms: foreign body sensation, burning, difficulty blinking, bruit on opening the eyelids, itching, eye fatigue, photophobia, blurred vision, and mucus extravasation at the inner canthi.

The treatment of this syndrome is based on the use of the following: tear substitutes whose task is the regular moisturizing of the cornea, but which do not exert any action on the basic causes of the disease and are endowed only with very short-lasting efficacy; inserts (plugs) in the lacrimal caniliculus; immunoregulators such as topical cyclosporin; topical steroids; anti-inflammatory agents (rumexilone and lotepredonl); autologous serum (cytokine inhibitors); topical or systemic androgens; mucus (HETE eicosanoid) and aqueous (P2Y2 agonists) secretogenic substances; acquaporins and agents such as antibiotics and detergents for the treatment of a disease often concomitant, blepharitis (*Cornea*, 2005; 24: 1-7).

Also used is treatment with iodide iontophoresis owing to its scavenger activity as a reducing agent and electron donor (*Adv. Clin. Path.*, 2000; 4: 11-17; *Br. J. Ophthalmol.*, 2005; 89: 40-44).

Even these latter treatments, despite exerting an action which may be regarded as more relevant to treating the causes of the disease, have failed to yield the anticipated results.

The normal transparency of the corneal surface can be impaired by the aftermath of numerous diseases acquired, degenerative or congenital that damage the delicate structure of the various constituent components. The acquired disease conditions most commonly implicated are post-keratitis damage, particularly after herpetic keratitis, and damage occurring in the aftermath of trauma and laser refractive surgery. The minimum common denominator is the formation of corneal opacities (leucomas) that functionally jeopardise vision. The events involved in wound healing that occur in the corneal tissue after infection, caustic damages, injury and refractive ablative surgery are have a profound effect on the final morphological and refractive outcomes of the restitutio ad integrum process.

The acute epithelial and stromal corneal lesions occurring immediately after injury and laser ablation are probably involved in the regulation of the subsequent corneal tissue repair events, and, among the latter, keratocyte apoptosis probably plays a major role (*Cornea*, 2000; 19:S7-12). This event is responsible for the corneal repair process since keratocyte apoptosis is the prime mover of the reproliferative stimulus. The stroma keratocytes underlying the initial acellular stroma therefore represent the cell source that mediates the subsequent healing of the surface stroma beneath the epithelium. As a result of the cellular repopulation, the activated keratocytes undergo myofibroblastic transformation (*Invest. Ophthalmol. Vis. Sci.*, 1998; 39:487-501), thus proving responsible for the production of collagen fibres and of basic substances involved in the restituito ad integrum process.

A recent scar is very similar to fetal tissue, it is rich in fetal and type III collagen with thick fibrils, wide interfibrillary spaces and a hydrophilic stroma. This explains the characteristic opacity. It also contains fibrinogen, fibronectin, laminin and weakly sulphurized keratan sulphate. The keratan sulphate/condroitin sulphate is reduced in the scar stroma.

The myofibroblasts disappear in a few weeks to a few months. Gradually the scar changes and becomes less opaque. The resistance of the stromal scar tissue is 20% compared with normal tissue after three weeks, 60% after 1 year and 70% after 3-4 years. Corneal reinnervation is very slow. The cytokines play an important role in these events. IL-1a, produced by the corneal epithelium, stimulates metalloprotease and collagenase synthesis through the keratocytes and the myofibroblasts. The TGF-β reduces the production of collagenase and is involved in the formation of haze. IL-6 reduces the synthesis of metalloprotease thus increasing collagen synthesis.

This process, however, is not self-controlled and, in many cases, abnormal, excessive healing occurs followed by a greater production of collagen type III, an increase of jaluronic acid, and an increase in lamellar disorganisation (*Arch. Ophthalmol.*, 1990; 108: 665-675; *Exp. Eye Res.*, 2004; 78: 553-560; *Ophthalmology*, 2000; 107: 1235-1245) or an accumulation of keratocytes and myofibroblasts as shown by confocal microscopy (*Progr. Retin. Eye Res.*, 1999; 18:311-356; *J. Cataract Refract. Surg.*, 2000; 26: 432-447; *Exp. Eye Res.*, 2004; 78: 553-560).

These abnormalities are involved in the pathogenesis of the most feared complication of stromal regeneration after photorefractive keratectomy (PRK), namely, haze, with consequent impairment of the functional outcome. Haze is classified according to Heitzmann in 5 degrees on the basis of the visual impairment due to the reduced corneal transparency (*Ophthalmology*, 1998; 35: 1411-1421); or according to the Fantes scale (*Arch. Ophthalmol.*, 1990; 108: 665-675) which distinguish 6 degrees of haze (0; 0.5; 1+; 2+; 3+; and 4+). Though the incidence of haze has been substantially reduced over recent years, as a result of the technological advances in the field of excimer lasers, it is still a fairly frequent complication even today and, in rare cases, would appear hard to reverse, even after months of cortisone therapy (0.5% of the eye with myopia not exceeding 6 diopters and 3-17% in the eye with myopia exceeding 10 diopters (Ophthalmol. Clin. North. Am., 2001, 14: 359-376). In cases of persistent haze (more than 15-18 months) which fails to respond to medical cortisonic therapy [an event that can occur with late-onset haze (4-12 months after the operation (*Ophthalmology*, 1997; 104: 369-374; *Cornea*, 2004, 23: 350-355), as the only feasible procedure is phototherapeutic keratectomy (PTK) with an excimer laser, a procedure used for the laser-assisted surgical removal of superficial stromal opacities combined with 0.02% mitomycin (J. Refract. Surg., 2003; 19:40-43; J. Refract Surg., 2003, 19:449-454). The use of the activator of plasminogen and of TGF-α1 is still undergoing animal studies (J. Refract. Surg., 1997; 13:356-361; Invest. Ophthalmol. Vis. Sci., 2004; 45:1329-1333), while INFβ-2b, tested on man, has produced poor results (J. Refract. Surg., 1996; 22:891-900).

Indeed, while low degree haze is generally asymptomatic, or only causes a slight reduction in sensitivity to contrast, serious forms of haze can interfere with refraction and be accompanied by myopic regression due to exuberant scarring (J. Refract. Surg., 1995; 11.341-347; Ophthalmology, 2000; 107:1235-1245).

The corneal dystrophies (Bietti, 1971; Oftalmologia geriatrica) are rare disorders. They are defined as primitive corneal disorders not associated with trauma, earlier inflammation or systemic diseases. They affect both eyes, are hereditary and, for the most part, have an autosomal dominant trait.

Corneal degeneration is far more common than dystrophies but the symptoms are generally less obvious. It is not hereditary, can be unilateral or bilateral and the course is gradual or relatively stable. In each case, it is, by definition, permanent, or does not resolve itself spontaneously.

Usually it involves more than one layer of the cornea. Distinctions can be drawn between primary or idiopathic and secondary forms. The first are often connected with ageing without being preceded by any specific pathological process, the second ones are always associated with eye diseases which precede them, whether acute, chronic, infectious or inflammatory in nature. Keratoconus is one of the most typical degenerative diseases.

Keratoconus is a non-inflammatory ectasia of the paracentral portion of the cornea which evolves over time and takes a progressively conical form, with tapering of the tip. This corneal deformation results in severe astigmatism, often irregular, corrected wherever possible with hard gas-permeable corneal lenses. Only rarely are epikeratoplasty, photorefractive keratectomy or the use of intracorneal rings (IN-TACTS) considered (*Cornea*, 1987; 6:131-139;

Ophthalmology, 1992; 99:1187-1192; Surv. Ophthalmol., 1998; 42:297-319; J. Cataract. Surg., 2000; 26: 1117-1122; J. Refract. Surg., 2001; 17:69-73) or also the use of hard gas-permeable lenses combined with INTACTS. All these techniques only correct the refractive defects but do not resolve the cause of the corneal ectasia and therefore do not stop the progress of keratoconus, which in its most severe form means a corneal transplant (Cornea, 1997; 16:623-629; Cornea, 1997; 16:414-419; Cornea, 1998; 17:468-470; Cornea, 2002; 21:152-155).

Keratoconus starts at puberty and in 20% of cases perforating keratoplasty has to be performed (Ophthalmology, 1994; 101: 439-447).

Past studies have not produced relevant results leading to an understanding of the physiopathology of the disease but only more recently, with the development of molecular techniques, have advances been made in understanding this abnormality.

At present, however, we are not able to say that the presence of keratoconus is due to uniform anomalies which are specific to the extracellular matrix. There are areas where the elements of the basal membrane are absent indicating on-going proteolytic activity, and there are areas in which there are deposits of fibrotic substance which is also found in other pathologies. A cornea with keratoconus has low levels of inhibitory enzymes (TIMP) and greater activity of the enzymes which are capable of degrading the extracellular matrix. The TIMP play a predominant role in the thickness of the stroma and in the stability of Bowman's membrane, which is characteristically interrupted in keratoconus. Furthermore the decrease in one of these inhibitors, TIMP-1, could play an important role in apoptosis or in the anomalous behaviour of the cells found in keratoconus.

Apoptosis is the programmed death of the cells. This death is necessary for reconstructing damaged cells and for the normal turn-over of many tissues.

In keratoconus, apoptosis is more frequently found in the stroma (Invest. Ophthalmol. Vis. Sci., 1998; 39: 220-226) than in other corneal layers (Cornea, 2002; 21: 206-209).

This observation is important because a cornea with keratoconus is subject to chronic irritation caused by hard gas-permeable contact lenses, to greater friction and to moderate or severe atrophy. Wilson suggests that mechanical trauma on the epithelium could cause apoptosis in the stromal cells of keratoconus (Exp. Eye Res., 1999; 69: 225-266; Cornea, 2000; 19: S7-S12). Furthermore, an increase in the levels of leukocytes commonly correlated to the LAR protein antigen present in keratoconus but not in normal corneas can be seen (Exp. Eye Res., 1999; 68:283-293).

LAR is a transmembrane phosphotyrosine transferase capable of stimulating apoptosis (Proc. Nati. Acad. Sci. USA, 1994; 91:10868-10872; J. Neurobiol., 2000; 42:477-486). A third triggering mechanism of apoptosis is that it is inhibited by TIMP-1 (J. Clin. Invest., 1998; 102:2002-2010; Blood, 1998; 92:1342-1349) which in keratoconus proves to be reduced, as has been reported previously.

In practice, given these statements, the phenomenon of apoptosis could play an important role in the pathogenesis of keratoconus.

Sodium hyaluronate is a very well known compound used to protect corneal epithelial cells, especially in patients with dry eye syndrome or with Sjögren's syndrome. The action of sodium hyaluronate is due not only to its protective role of a mechanical type exerted on the epithelial cells as a result of its viscoelasticity, in situations of reduced tear production, but also to the positive effects of its particular biological function on corneal epithelial cells by stimulating their migration (*Exp. Eye Res.*, 1991; 53:753-758).

Taurine (or 2-aminoethanesulphonic acid) is considered an amino acid, even though it does not possess the characteristic carboxyl group (COOH) but the $SO_3H$ group. Taurine is only present in the animal realm, whereas vegetable foods do not possess this amino acid.

Vitamin E is the main antioxidant of the cell membranes, and is found in the human body in 4 forms consisting of $\alpha$-tocopherol, $\beta$-tocopherol, $\gamma$-tocopherol and $\delta$-tocopherol. Of these the $\alpha$ form is the most frequent in the retina and in plasma and is the one with the greatest antioxidant and free radical scavenging activity.

Vitamin A is essential for cell vitality, cytoskeletal organisation, it regulates the expression of proteins of the extracellular matrix, cell adhesion and wound repair (J. Cell. Biochem., 2003; 89: 837-847). Vitamin A is also involved in the production of angiogenic (inactivation) and anti-angiogenic (activation) factors in the endothelial cells (Exp. Eye Res., 2004; 78: 945-955). Some of these, stromal derived factor 1 (SDF-1) are secreted under the effect of proinflammatory signals (IL-1, TNF-$\alpha$, bacteria and viruses) and, in cooperation with other factors, are involved in the proliferation of the vascular endothelial cells. SDF-1 and its receptor CXCR4 have been found in human keratocytes (Mol. Vis., 2003; 9:96-102). Two other systems are also involved in corneal angiogenesis: vascular endothelial growth factor (VEGF) and fibroblast growth factor b (b FGF). Anti-angiogenetic factors contrast these cytokines as the pigment epithelium derived factor (PEDF) (Mol. Vis., 2001, 7: 154-163). IL-4 and TGF-$\beta$ are also known to inhibit corneal angiogenesis in vivo (Acta Ophthalmol. Scand., 2002; 80:238-247). Metalloproteases are able to intervene in the regulation of angiogenesis with inhibitory or potentiating effects. In the absence of vitamin A, the corneal epithelium becomes keratinised. Retinol and retinic acid (Vitamin A), which help to avoid the keratinisation of the corneal epithelium, are supplied by the tears. Nuclear receptors with retinoids are present in the epithelium and in the stroma.

Cytidine-5'-diphosphate choline (CDP-choline), commonly known by the name of citicoline, is a precursor of phosphatidyl choline, the main phospholipid of the cell membranes. Due to the effect of the activation of certain lytic enzymes, the phospholipases, the catabolism of the membrane phospholipids is accelerated and, if the resynthesis mechanism is inadequate, toxic substances accumulate, such as the ceramides, which can activate the metabolic pathways which lead to cell apoptosis. A deterioration in the turn-over of the phospholipids adversely affects the validity of the membrane protection systems and puts cell function at risk.

The use of inorganic elements is well known in the medical field, and a number of these are essential for the stability of the tear film (Pescosolido 2000).

Previous uses of carnitine in the ophthalmological field are already known.

U.S. Pat. No. 5,037,851 describes the use of acetyl L-carnitine for the treatment of cataracts.

U.S. Pat. Nos. 5,145,871 and 5,432,199 describe the use of acetyl D-carnitine for the treatment of glaucoma.

U.S. Pat. No. 5,883,127 describes the use of acetyl L-carnitine for the treatment of maculopathy and macular degeneration.

Further uses of carnitine are also known.

In Res 1992; 18(8):355-365 the use of L-carnitine in the cardiological field is described.

U.S. Pat. No. 5,543,556 describes the use of acyl L-carnitine esters with gamma-hydroxybutyric acid for the inhibition of neuronal degeneration and in the treatment of coma.

U.S. Pat. No. 5,811,457 describes the use of propionyl L-carnitine for the treatment of chronic obliterating arteriopathy.

None of the above-cited patents or publications describes or suggests the use of L-carnitine or of alkanoyl L-carnitine for the treatment of diseases of the cornea.

In the medical field there is still a strongly perceived need for the availability of therapeutic agents or physiological supplement useful for the treatment of the above-mentioned corneal diseases.

SUMMARY OF THE INVENTION

Detailed Description of the Invention

It has now been found that L-carnitine and/or one or more alkanoyl L-carnitines, or one of their pharmaceutically acceptable salts, are useful agents for the preparation of an hypo-osmolal physiological supplement or medicament, in the form of eye-drops, for the treatment of diseases of the cornea.

What is meant by pharmaceutically acceptable salt of L-carnitine is any salt of the latter with an acid that does not give rise to toxic or side effects.

These acids are well known to pharmacologists and to experts in pharmacy. Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

What is meant by pharmaceutically acceptable salt of L-carnitine is also a salt approved by the FDA and listed in the publication Int. J. of Pharm. 33 (1986), 201-217, which is incorporated herein by way of a reference.

One object of the present invention is the use of L-carnitine and/or of one or more alkanoyl L-carnitines selected from the group consisting of acetyl, propionyl, valeryl, isovaleryl, butyryl and isobutyryl L-carnitine, or one of their pharmaceutically acceptable salts, for the preparation of an ophthalmic physiological supplement or a medicament in the form of eye-drops, having an osmolality broadly in a range of about 50 to about 250 mOsmols/kg, for the treatment of corneal diseases. Some preferred aspects of the invention include eye-drops having an osmolality in a range of about 100 to about 200 mOsmols/kg. More preferably, the eye drops have an osmolality in a range of about 120 to about 1400 mOsmols/kg. Still more preferably, the eye drops have an osmolality of about 125 mOsmols/kg.

Examples of the corneal diseases include for example and without limitation, de-epithelializing diseases, dry eye syndrome; infective keratitis; acid or alkaline caustic damages; corneal abrasions and/or injuries due to mechanical action or contact lenses; degenerative disease of the corneal stroma such as acute or chronic keratoconus, stromal damages caused by refractive laser surgery; and dystrophic diseases, impairment of the transparency of the surface of the cornea caused by various types of infective keratitis (viral, bacterial and fungal), or by injuries that damage the structure of the various components constituting the cornea, such as, for instance, injuries of a mechanical, post-surgical and post-laser-refractive surgery type (such as, for example, haze); hereditary or degenerative diseases such as chronic and acute keratoconus.

A further object of the present invention is a physiological supplement or medicament for ophthalmic use, in the form of eye-drops, comprising as the active ingredient L-carnitine, or one of its pharmaceutically acceptable salts, in combination with humidifying agents such as sodium hyaluronate; antioxidants such as vitamin E; inorganic elements as components of enzymes present in the tear film such as manganese; inorganic and organic elements such as sodium, potassium and taurine, and optionally ophthalmologically acceptable excipients and/or diluents;

in which:
  L-carnitine is present preferably at a dose of about 0.5 to about 2.5% by weight, and most preferably at a dose of about 1%;
  taurine is present preferably at a dose of about 0.1 to about 4% by weight, and most preferably at a dose of about 0.5%;
  sodium hyaluronate is present preferably at a dose of about 0.05 to about 1.5% by weight, and most preferably at a dose of about 0.2%;
  vitamin E is present preferably at a dose of about 0.05 to about 1.0% by weight, and most preferably at a dose of about 0.2%;
  manganese is present preferably at a dose of about 0.01 to about 0.1 mg/L, and most preferably at a dose of about 0.051 mg/L;
  zinc is present preferably at a dose of about 0.5 to about 1.5 mg/L, and most preferably at a dose of about 1.02 mg/mL;
  sodium is present preferably at dose of about 5 to about 5000 mg/L, and most preferably at a dose of about 30 mg/L;
  potassium is present preferably at a dose of about 1 to about 1000 mg/L, and most preferably at a dose of about 9 mg/L;
  and the osmolality is in a range of about 50 to about 250 mOsmols/kg, preferably in a range of about 100 to about 200 mOsmols/kg, more preferably in a range of about 120 to about 1400 mOsmols/kg and still more preferably about 125 mOsmols/kg. (the osmolality in the eye drops of the invention is due to predominantly by the presence of L-carnitine or a derivative thereof, the other components are almost irrelevant).

For purposes of the present invention, it will be understood by those of ordinary skill that the methods of treatment and use described herein are meant to include methods of treating human or animal eyes. Such methods include administering a medicament, for example, eye drops in accordance with the present invention, to a human or animal eye to provide medicinal benefit to the treated eye. The amount of the eye drops administered to the patient is generally described as an amount which is effect to treat, even temporarily and or symptomatically one or more of the conditions described herein. Thus the methods include administering 1 or more drops in the affected eye one or more times daily. The clinician of ordinary skill will, of course, be able to determine optimum dosing based on assessment of the clinical condition and strength of the ingredients included in the medicament.

Reference is made herein to medicaments in the form of eye drops. It should be understood that for purposes of the present invention that eye drops include solutions, suspensions, gels, creams and ointments intended for ophthalmic use.

The eye-drops according to the present invention may additionally contain further antioxidants, vitamins, Borage oil; epithelializing and anti-angiogenic agents; humidifying agents; inorganic elements; regulators of the cellular osmolality; antibiotics; anti-inflammatory agents, antiviral and antifungal agents. Such other components which may be included in the medicaments of the present invention may further include, without limitation, buffering agents, tonicity adjusting agents, ophthalmically acceptable preservatives, pH adjusting agents, components commonly found in artificial tears, such as one or more electrolytes, and the like and mixtures thereof. It will be further understood that all ingredients included in the medicaments of the present invention are preferably ophthalmically acceptable and can be chosen from materials which are conventionally employed in ophthalmic compositions, for example, compositions used to treat eyes afflicted with dry eye syndrome, artificial tear formulations and the like.

The term "ophthalmically acceptable" with respect to a formulation, medicament, composition or ingredient herein means having no persistent detrimental effect on the treated eye or the functioning thereof, or on the general health of the subject being treated. It will be recognized that transient effects such as minor irritation or a "stinging" sensation are common with topical ophthalmic administration of drugs and the existence of such transient effects is not inconsistent with the formulation, composition or ingredient in question being "ophthalmically acceptable" as herein defined. However, preferred formulations, medicaments, compositions and ingredients are those that cause no substantial detrimental effect, even of a transient nature.

Aside from the amounts for each of the ingredients described herein, it will be understood that the compositions will include amounts generally understood in the art as being effective concentrations for such ingredients and as readily apparent to those of ordinary skill.

The following examples illustrate the invention.

EXAMPLE 1

A clinical trial was conducted in which 43 patients suffering from dry eye syndrome were recruited.

The patients recruited were all women aged from 35 to 77 years (mean age: 59.5±10.4 years), 33 of whom were suffering from Sjögren's syndrome, diagnosed on the basis of Fox et al.'s criteria (*Arthritis Rheum,* 1986; 29: 577-584; 1986).

Patients were selected on the basis of the BUT test, the Schirmer test, the fluorescein test and the rose bengal test (*Pescosolido* 2000; *Arch. Ophthalmol.,* 1969; 82: 10-14).

The BUT test had to yield results ≦5 seconds, while the Schirmer test did not contraindicate inclusion in the trial.

Damage to the surface of the eye was evaluated by means of the rose bengal staining test and the fluorescein test. Damage in the rose Bengal staining test was determined by reference to the van Bijsterveld evaluation (*Arch. Ophthalmol.,* 1969; 82: 10-14), dividing the exposed surface into 3 zones, with a score of 0 to 3 per zone.

For abnormality of the fluorescein test score both the affected surface (A) and the damage density (D) were evaluated, with a range from 0 to 3 (low and high) on the basis of severity *Jap. Clin. Ophthalmol.;* 1994; 48: 183-188).

On the basis of the test score results, patients were divided into 3 subgroups, namely, those with mild dry eye (A1D1, A1D2, A2D1), those with moderate dry eye (A1D3, A2D2, A3D1) and those with severe dry eye (A2D3, A3D2, A3D3).

The right eye ® of patients was treated with the eye-drops according to the invention, consisting of 1% L-carnitine, 0.5% taurine, 0.2% sodium hyaluronate, 0.2% water-soluble vitamin E, 1.02 mg/L zinc, 0.051 mg/L manganese, 30 mg/L sodium, and 9 mg/L potassium (osmolality of about 125 mOsmols/kg).

The left eye (L), which served as the control eye, the baseline values of which were no different from those of the right eye ®, was treated with 0.2% hyaluronic-acid-based eye-drops.

Treatment efficacy was determined after 30 days, 4 hours after the last treatment.

The results obtained are presented in Tables 1-3.

TABLE 1

| Dry eye | | BUT test (sec) | | P < vs | P < vs Left eye (End of |
|---|---|---|---|---|---|
| | | Base-line | End of treatment | base-line | treatment) |
| Mild | Right eye ® | 3.1 ± 1.6 | 7.3 ± 1.2 | P < 0.001 | P < 0.001 |
| | Left eye (L) | 2.8 ± 1.4 | 4.1 ± 1.5 | | |
| Moderate | R | 1.7 ± 1.1 | 5.5 ± 1.5 | P < 0.001 | P < 0.001 |
| | L | 1.5 ± 1.3 | 1.9 ± 1.2 | | |
| Severe | R | 1.0 ± 1.0 | 4.6 ± 1.7 | P < 0.001 | P < 0.001 |
| | L | 0.8 ± 1.2 | 1.2 ± 1.0 | | |

Each entry represents the mean ± standard deviation.

TABLE 2

| Dry eye | | Rose bengal test (score) | | P < vs | P < Vs Left eye (end of |
|---|---|---|---|---|---|
| | | Baseline | End of treatment | base-line | treatment) |
| Mild | R | 3.7 ± 1.9 | 2.5 ± 1.2 | P < 0.001 | P < 0.01 |
| | L | 3.5 ± 1.7 | 3.5 ± 1.8 | | |
| Moderate | R | 4.7 ± 2 | 3.1 ± 2 | P < 0.001 | P < 0.01 |
| | L | 4.5 ± 2.2 | 4.4 ± 2 | | |
| Severe | R | 5.9 ± 2.6 | 4.5 ± 2.3 | P < 0.01 | P < 0.05 |
| | S | 6.1 ± 2.5 | 5.6 ± 2.4 | | |

Each entry represents the mean ± standard deviation.

TABLE 3

| Dry eye | | Schirmer test (mm) | | P < vs | P < Vs Left eye (end of |
|---|---|---|---|---|---|
| | | Baseline | End of treatment | baseline | treatment) |
| Mild | R | 11.5 ± 11.4 | 12.2 ± 5.1 | NS | NS |
| | L | 11.3 ± 10.0 | 11.2 ± 9.0 | | |
| Moderate | R | 5.8 ± 6.4 | 7.2 ± 4.3 | NS | NS |
| | L | 5.6 ± 6.6 | 7.0 ± 5.5 | | |
| Severe | R | 3.7 ± 3.8 | 5.3 ± 2.4 | P < 0.05 | P < 0.05 |
| | L | 3.4 ± 4.1 | 4.2 ± 2.6 | | |

Each entry represents the mean ± standard deviation.

EXAMPLE 2

In this clinical trial the patient sample recruited consisted of 16 patients, 8 men and 8 women, ranging in age from 21 to 32 years (mean age: 25±4.2 years), who had been submitted to refractive laser surgery (PRK) in both eyes with myopia not exceeding 6 diopters.

The right eye ® was treated for 3 months with the eye-drops according to the present invention, while the left eye (L), which served as a control, was treated with 0.2% hyaluronic-acid-based eye-drops. Both eyes were treated with antibiotic eye-drops for 5 days. A surface cortisonic was also administered in the left eye 5 days after the operation for 3 months.

The efficacy of adequate re-epithelialisation after PRK was evaluated by means of biomicroscopy and the contrast sensitivity test.

Biomicroscopy was performed with first vertical and then horizontal light target orientation, after 2, 3, 5 and 7 days of treatment, calculating the de-epithelialisation area.

For the purposes of evaluating the optimal result after PRK, denoting normal re-epithelialisation and stromal repair, the contrast sensitivity test was performed (*Pescosolido N., Guida automobilistica ed efficacia visiva; Canelli (AT), Fabiano Ed.*, 2001; hereinafter this reference will be referred to as *Pescosolido* 2001).

Since the vision of an object or image cannot be limited to minimum separable perception (visual acuity), one important parameter evaluated was the contrast of the object. To study this parameter, the perception threshold was measured for a whole range of objects of various sizes with increasingly reduced contrasts. The resulting assessment was the spatial contrast sensitivity function (spatial CSF) (*Pescosolido* 2001). For this function, test images were mainly used consisting of stripes with a sinusoidal luminance profile. These bars, alternating dark and light, were defined by their spatial frequency [cycles per degree (CPD) or number of pairs of stripes (black/white) per degree of visual angle] and by their contrast. The inverse of contrast Ⓒ was contrast sensitivity (S) (S=1/C). Contrast is often expressed in terms of percentages, 98% being very high, and 3% very low (*Pescosolido* 2001).

The contrast sensitivity test was performed using the Optec 6500 vision tester capable of receiving ETDRS and FACT test scores and software for the management and analysis of contrast sensitivity data. The system was capable of simulating the way in which the patient actually saw things. Moreover, it was capable of comparing patient simulations with standard representations. The examination was performed first after 10 days and then at 3 and 6 months postoperatively. Patients started treatment immediately after PRK. The right eye Ⓡ was treated with the eye-drops according to the present invention mentioned in example 1 (2 drops, 4 times daily), while the left eye, which served as a control, was treated with 0.2% hyaluronic-acid-based eye-drops and surface cortisonic after postoperative day 5 (the latter only for the first 3 months, 3 times daily).

Single-dose antibiotic eye-drops was instilled in both eyes 4 times daily and a hydrogel contact lens was applied to both eyes after PRK for the first 5 days postoperatively.

Two days after the operation (PRK) the patients treated with the eye-drops according to the present invention presented a de-epithelialization area of 6.0 mm²±6.8 mm, whereas in the control eyes the de-epithelialization area measured 8.4 mm²±9.2 mm. After 3 days complete re-epithelialization in the treated eyes was 77% as against 61% in the control eyes. After 5 days complete re-epithelialization was 100% as against 90% in the control eyes. After 7 days re-epithelialization was 100% in both eyes.

Evaluation of the variation in contrast after 6 months' treatment in the eyes treated with the eye-drops according to the present invention Ⓡ compared to the control eyes (L) showed a statistically significant difference.

The results obtained are presented in Table 4.

TABLE 4

| Time | Eye examined | Contrast (%) | P < vs L |
|---|---|---|---|
| Baseline | R | 96 ± 2 | NS |
|  | L | 96 ± 2 |  |
| After 6 months | R | 90 ± 3 | P < 0.001 |
|  | L | 78 ± 6 |  |

Each entry represents the mean ± standard deviation.

L-carnitine and its alkanoyl derivatives are known compounds, the preparation process for which is described in U.S. Pat. No. 4,254,053.

The physiological supplement or medicament according to the present invention may be bought with or without medical prescription.

The physiological supplement or medicament according to the present invention are composed of active ingredients which are familiar to operators in the medical field and already in use in clinical practice, and their pharmacotoxicological profiles are known.

Their procurement therefore is very easy, inasmuch as these are products which have been on the market now for a long time and are of a grade suitable for human or animal administration.

In the following are reported non limiting examples of compositions according to the present invention.

Eye-drops 1
L-carnitine 0.5%;
Taurine 0.5%;
sodium hyaluronate 0.2%;
vitamin E 0.2%;
manganese 0.051 mg/L;
zinc 1.02 mg/L;
sodium 30 mg/L;
potassium 9 mg/L;
Sodium mertiolate 0.02 mg/mL;
Demineralized water;
Volume 5 mL/vials.
Osmolality of about 50 mOsmols/kg.

Eye-drops 2
L-carnitine 1%;
Taurine 0.5%;
sodium hyaluronate 0.2%;
vitamin E 0.2%;
manganese 0.051 mg/L;
zinc 1.02 mg/L;
sodium 30 mg/L;
potassium 9 mg/L;
Sodium mertiolate 0.02 mg/mL;
Demineralized water;
Volume 5 mL/vials.
Osmolality of about 125 mOsmols/kg.

Eye-drops 3
L-carnitine 1.5%;
Taurine 0.5%;
sodium hyaluronate 0.2%;
vitamin E 0.2%;
manganese 0.051 mg/L;
zinc 1.02 mg/L;
sodium 30 mg/L;
potassium 9 mg/L;
Sodium mertiolate 0.02 mg/mL;
Demineralized water;
Volume 5 mL/vials.
Osmolality of about 150 mOsmols/kg.

Eye-drops 4

L-carnitine 2%;
Taurine 0.5%;
sodium hyaluronate 0.2%;
vitamin E 0.2%;
manganese 0.051 mg/L;
zinc 1.02 mg/L;
sodium 30 mg/L;
potassium 9 mg/L;
Sodium mertiolate 0.02 mg/mL;
Demineralized water;
Volume 5 mL/vials.
Osmolality of about 200 mOsmols/kg.

Eye-drops 5
L-carnitine 2.5%;
Taurine 0.5%;
sodium hyaluronate 0.2%;
vitamin E 0.2%;
manganese 0.051 mg/L;
zinc 1.02 mg/L;
sodium 30 mg/L;
potassium 9 mg/L;
Sodium mertiolate 0.02 mg/mL;
Demineralized water;
Volume 5 mL/vials.
Osmolality of about 250 mOsmols/kg.

The invention claimed is:

1. A physiological supplement or medicament for ophthalmic use, in the form of eye-drops, comprising:
   L-carnitine 0.5-2.5%;
   Taurine 0.1-4%;
   sodium hyaluronate 0.05-1.0%;
   vitamin E 0.05-1.0%;
   manganese 0.01-0.1 mg/L;
   zinc 0.5-1.5 mg/L;
   sodium 5-5000 mg/L;
   potassium 1-1000 mg/L; and
   osmolality in a range of about 50-250 mOsmols/kg.

2. The eye-drops of claim 1, further comprising one or more ophthalmologically acceptable excipients or diluents or mixtures thereof.

* * * * *